US010219803B2

(12) United States Patent
Grant et al.

(10) Patent No.: US 10,219,803 B2
(45) Date of Patent: Mar. 5, 2019

(54) SURGICAL INSTRUMENT

(71) Applicants: Ryan Grant, Branford, CT (US);
Michael Diluna, New Haven, CT (US);
Vadim Gordin, Louisville, KY (US)

(72) Inventors: Ryan Grant, Branford, CT (US);
Michael Diluna, New Haven, CT (US);
Vadim Gordin, Louisville, KY (US)

( * ) Notice: Subject to any disclaimer, the term of this patent is extended or adjusted under 35 U.S.C. 154(b) by 299 days.

(21) Appl. No.: 15/057,126

(22) Filed: Mar. 1, 2016

(65) Prior Publication Data

US 2017/0252034 A1 Sep. 7, 2017

(51) Int. Cl.
| *A61B 17/04* | (2006.01) |
| *A61B 17/062* | (2006.01) |
| *A61B 17/00* | (2006.01) |
| *A61B 17/06* | (2006.01) |
| *A61B 17/29* | (2006.01) |

(52) U.S. Cl.
CPC ...... *A61B 17/0469* (2013.01); *A61B 17/0625* (2013.01); *A61B 2017/00367* (2013.01); *A61B 2017/00398* (2013.01); *A61B 2017/00535* (2013.01); *A61B 2017/00876* (2013.01); *A61B 2017/0609* (2013.01); *A61B 2017/2929* (2013.01)

(58) Field of Classification Search
CPC ............ A61B 17/0625; A61B 17/0469; A61B 2017/047; A61B 2017/0477; A61B 17/062
See application file for complete search history.

(56) References Cited

U.S. PATENT DOCUMENTS

| 5,176,691 A | 1/1993 | Pierce |
| 5,192,287 A | 3/1993 | Fournier |
| 5,250,054 A | 10/1993 | Li |
| 5,320,632 A | 6/1994 | Heidmueller |
| 5,368,601 A | 9/1994 | Sauer |
| 5,403,329 A | 4/1995 | Hinchcliffe |
| 5,417,699 A | 5/1995 | Klein |
| 5,527,321 A | 6/1996 | Hinchliffe |
| 5,573,542 A | 10/1996 | Stevens |
| 5,628,758 A | 5/1997 | Often |
| 5,797,929 A | 8/1998 | Andreas |
| 6,051,006 A | 4/2000 | Schuzas |
| 6,716,224 B2 | 4/2004 | Singhatat |
| 6,743,241 B2 | 6/2004 | Kerr |
| 6,939,357 B2 | 9/2005 | Navarro |
| 7,060,007 B2 | 6/2006 | Gordon |
| 7,390,328 B2 | 6/2008 | Modesitt |
| 7,850,701 B2 | 12/2010 | Modesitt |
| 8,162,962 B2 | 4/2012 | Poo |
| 8,202,281 B2 | 6/2012 | Voss |
| 8,252,008 B2 | 8/2012 | Ma |
| 8,267,947 B2 | 9/2012 | Pantages |
| 8,348,962 B2 | 1/2013 | Nobles |
| 8,366,725 B2 | 2/2013 | Chu |
| 8,449,559 B2 | 5/2013 | Keren |
| 8,562,629 B2 | 10/2013 | Bain |
| 8,597,309 B2 | 12/2013 | Stafford |
| 2007/0282354 A1 | 12/2007 | McIntosh |

(Continued)

*Primary Examiner* — Todd Scherbel
*Assistant Examiner* — Brooke Labranche

(57) ABSTRACT

Disclosed herein are devices capable of (1) gasping tissue, (2) passing suture through the tissue, and (3) resetting both their tissue grasping and suture passing features without the device being removed from the incision.

18 Claims, 12 Drawing Sheets

(56) References Cited

U.S. PATENT DOCUMENTS

| | | | |
|---|---|---|---|
| 2009/0177031 A1* | 7/2009 | Surti | A61B 1/00087 600/106 |
| 2012/0277768 A1* | 11/2012 | Viola | A61B 17/0469 606/145 |
| 2013/0012962 A1 | 1/2013 | Stone | |
| 2013/0066340 A1 | 3/2013 | Pantages | |

* cited by examiner

SURGICAL INSTRUMENT

CLAIM OF PRIORITY

This is the first filing made with the USPTO by the applicant regarding the present disclosure.

BACKGROUND/FIELD

In the field of minimally invasive spine surgery, it is often the case that the fascia must be closed through small diameter (less than 5 cm diameter) incisions. Particularly with patients having high BMI, this can often prove to be difficult using existing tools as there is often not enough room for separate instruments to grab tissue, rotate and angle instruments, push suture through the tissue, and throw sutures.

Disclosed herein are devices capable of (1) gasping tissue, (2) passing suture through the tissue, and (3) resetting both their tissue grasping and suture passing features without the device being removed from the incision.

SUMMARY

According to certain embodiments of the present disclosure, a surgical tool includes, at least a first and second jaw having complementary faces sized and shaped for grasping tissue therebetween wherein the distance between the jaws may be modulated between a shorter-distance "closed" condition and a longer distance "open" condition; an elongated needle selectably engageable to at least one of the jaws, wherein the needle has a first joining structure selected from one of a detent, emboss, or groove disposed about a portion of the circumference near the first end the needle; there is a complimentary opening in the first jaw sized and shaped to accommodate the first end of the needle therein and a capturing structure disposed upon a portion of the circumference of the opening, with the capturing structure being sized and shaped to have a substantially inverse shape to that of the first joining structure so as to enable mechanical coupling between the capturing structure to the first joining structure; wherein rotating the needle about the long axis of the needle into a configuration henceforth referred to as "A" with the first joining structure and first capturing structure interfering with one another couples the first end of the needle to the first jaw; wherein rotating the needle about the long axis of the needle into a configuration henceforth referred to as "B" with the first capturing structure obscured from the first joining structure disengages the respective capturing and joining structures from one another and consequently disengages the needle from the first jaw.

According to further embodiments of the present disclosure, the needle has a second joining structure selected from one of a detent, emboss, or groove disposed upon a portion of the circumference of the second end of the needle; wherein there is a complimentary opening in the second jaw sized and shaped to accommodate the second end of the needle therein and a capturing structure disposed upon a portion of the circumference of the opening, with the capturing structure being sized and shaped to have a substantially inverse shape to that of the second joining structure so as to enable mechanical coupling between the capturing structure to the second joining structure; wherein rotating the needle about the long axis of the needle into a configuration henceforth referred to as "C" with the second joining structure and second capturing structure interfering with one another couples the second end of the needle to the second jaw; wherein rotating the needle about the long axis of the needle into a configuration henceforth referred to as "D" with the second capturing structure obscured from the second joining structure disengages the respective capturing and joining structures from one another and consequently disengages the needle from the second jaw.

According to further embodiments of the present disclosure, the first end of the needle has at least one sloping face disposed away from the first joining structure and a complementary biasing member disposed within the first capturing structure such that when the surgical tool is oriented in a B configuration, the force of the biasing member against the sloped face urges the needle out of the first jaw.

According to further embodiments of the present disclosure, the distance between the jaws is adjustable by a user of the device by means of a mechanical, hydraulic, pneumatic, or electronic coupling.

According to further embodiments of the present disclosure, the first joining structure and second joining structure are substantially parallel to one another and the first and second joining structures are aligned to one another such that the A and C conditions occur contemporaneously and the B and D conditions occur contemporaneously such that disengaging the needle from the first jaw engages it upon the second jaw and vice versa.

According to further embodiments of the present disclosure, the first engagement structure and second engagement structure upon the needle are aligned to one another and there are respective clips in each jaw aligned to one another such that if the needle is rotated between the A condition and B condition it is always capable of being coupled to either the first or second jaw.

According to further embodiments of the present disclosure, there is stop disposed within the opening in the first jaw that limits the depth to which the first end of the needle may be interested therewithin.

According to further embodiments of the present disclosure, the engagement structure is selected from one of a magnet, a polymer spring, a metallic spring, live-hinged spring formed into the jaw, a planar u-shaped shackle, a recessed feature, an embossed feature, piano wire, or a single sided planar slip.

According to further embodiments of the present disclosure, there is a gear coupled to the first jaw and capable of rotating about the long axis of the needle, wherein the gear catches the needle within the opening and turns it when necessary between the A and B configurations.

According to further embodiments of the present disclosure, the gear is driven by a rotating shaft.

According to further embodiments of the present disclosure, the gear is driven by a flexible toothed rack gear that slides past complementary teeth on the needle gear.

According to further embodiments of the present disclosure, the gear is mechanically or electronically coupled to a stop such that it may only be turned when the jaws are configured into the "closed" condition.

According to a further embodiment of the present disclosure, the opening has a substantially u-shaped profile.

According to a further embodiment of the present disclosure, the opening is a substantially round aperture.

According to a further embodiment of the present disclosure, the jaws are at the distal end of an elongated shaft.

According to a further embodiment of the present disclosure, the jaws and needle are driven by mechanically coupled hand controls at the proximal end of the shaft.

According to a further embodiment of the present disclosure, the needle has an aperture extending through a medial portion thereof with the aperture sized and shaped to securely accommodate a portion of suture therewithin.

According to further embodiments of the present disclosure, the needle has a portion of suture fixed to a medial portion thereof.

According to certain embodiments of the present disclosure, a surgical tool includes, at least a first and second jaw having complementary faces sized and shaped for grasping tissue therebetween wherein the distance between the jaws may be modulated between a shorter-distance "closed" condition and a longer distance "open" condition; an elongated needle selectably engageable to at least one of the jaws, wherein the needle has a first joining structure selected from one of a detent, emboss, or groove disposed about a portion of the circumference near the first end the needle; there is a complimentary opening in the first jaw sized and shaped to accommodate the first end of the needle therein and a capturing structure disposed upon a portion of the circumference of the opening, with the capturing structure being sized and shaped to have a substantially inverse shape to that of the first joining structure so as to enable mechanical coupling between the capturing structure to the first joining structure; wherein rotating the first joining structure about the long axis of the needle into a configuration henceforth referred to as "A" with the first joining structure and first capturing structure interfering with one another couples the first end of the needle to the first jaw; wherein rotating the first joining structure about the long axis of the needle into a configuration henceforth referred to as "B" with the first capturing structure obscured from the first joining structure disengages the respective capturing and joining structures from one another and consequently disengages the needle from the first jaw.

According to certain embodiments of the present disclosure, a surgical tool includes; at least a first and second jaw having complementary faces sized and shaped for grasping tissue therebetween wherein the distance between the jaws may be modulated between a shorter-distance "closed" condition and a longer distance "open" condition; a needle selectably engageable within at least one of the jaws, wherein the needle has a first joining structure selected from one of a detent, emboss, or groove disposed upon a portion of the circumference of the first end the needle; and there is a complimentary opening in the first jaw sized and shaped to accommodate the needle therein and a capturing structure disposed upon a portion of the circumference of the opening, with the capturing structure being sized and shaped to have a substantially inverse shape to that of the first joining structure so as to enable mechanical coupling between the capturing structure to the first joining structure; wherein rotating the capturing structure about the long axis of the needle obscures the first capturing structure from the first joining structure, thereby disengaging the needle therefrom.

BRIEF DESCRIPTION OF THE FIGURES

In the figures, which are not necessarily drawn to scale, like numerals describe substantially similar components throughout the several views. The drawings illustrate generally, by way of example, but not by way of limitation, various embodiments discussed in the claims of the present document.

DETAILED DESCRIPTION OF THE FIGURES

Figure 1:
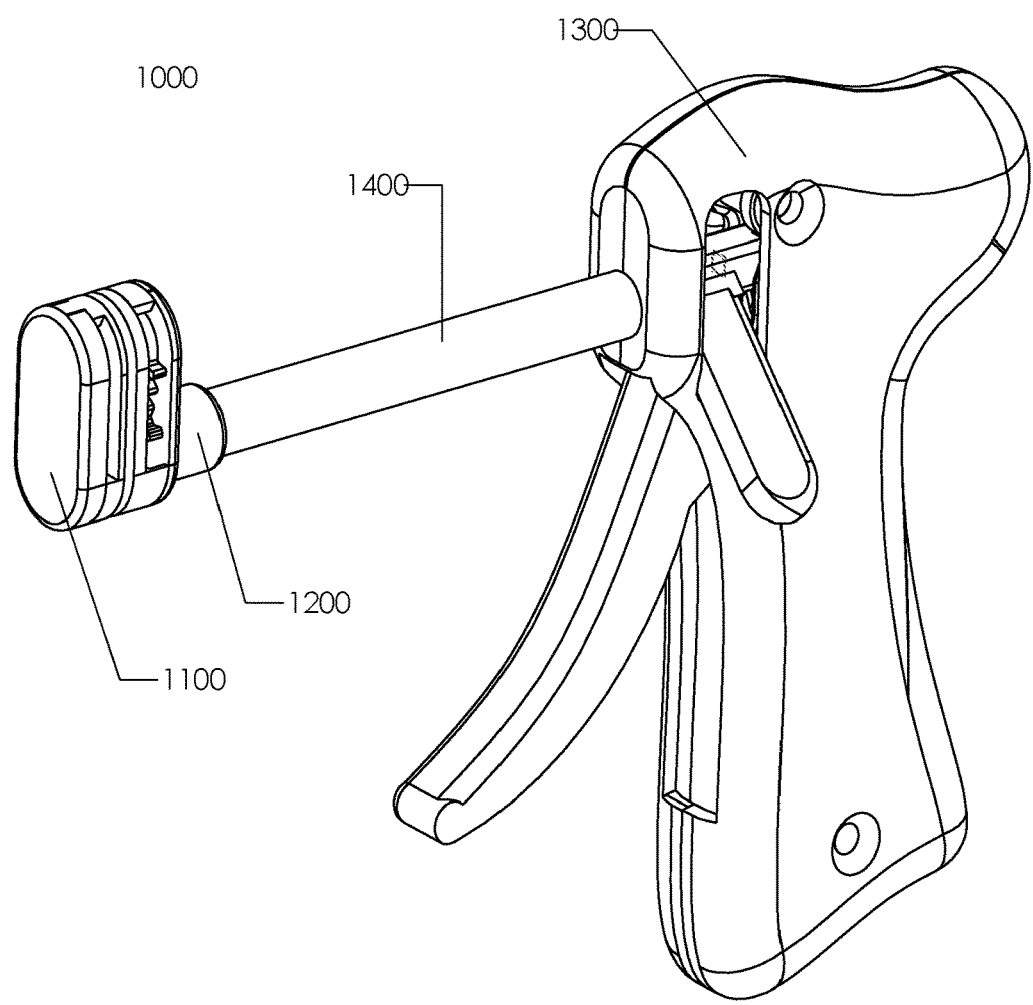
FIG. 1 shows a perspective view of a surgical tool 1000.

Various embodiments of the presently disclosed apparatus will now be described in detail with reference to the drawings, wherein like reference numerals identify similar or identical elements. In the drawings and in the description that follows, the term "proximal," will refer to the end of a device or system that is closest to the operator, while the term "distal" will refer to the end of the device or system that is farthest from the operator. Similar, anatomical terms of reference such as dorsal, lateral, anterior, and sagittal shall have their accepted meanings in the arts.

Referring now to FIG. 1, a first embodiment of the present disclosure 1000 of a surgical tool is shown. Surgical tool 1000 includes a handle 1300 having a shaft 1400 extending distally therefrom along with a fixed proximal jaw 1200 and a movable distal jaw 1100 disposed about the distal end of shaft 1400.

Figure 2:
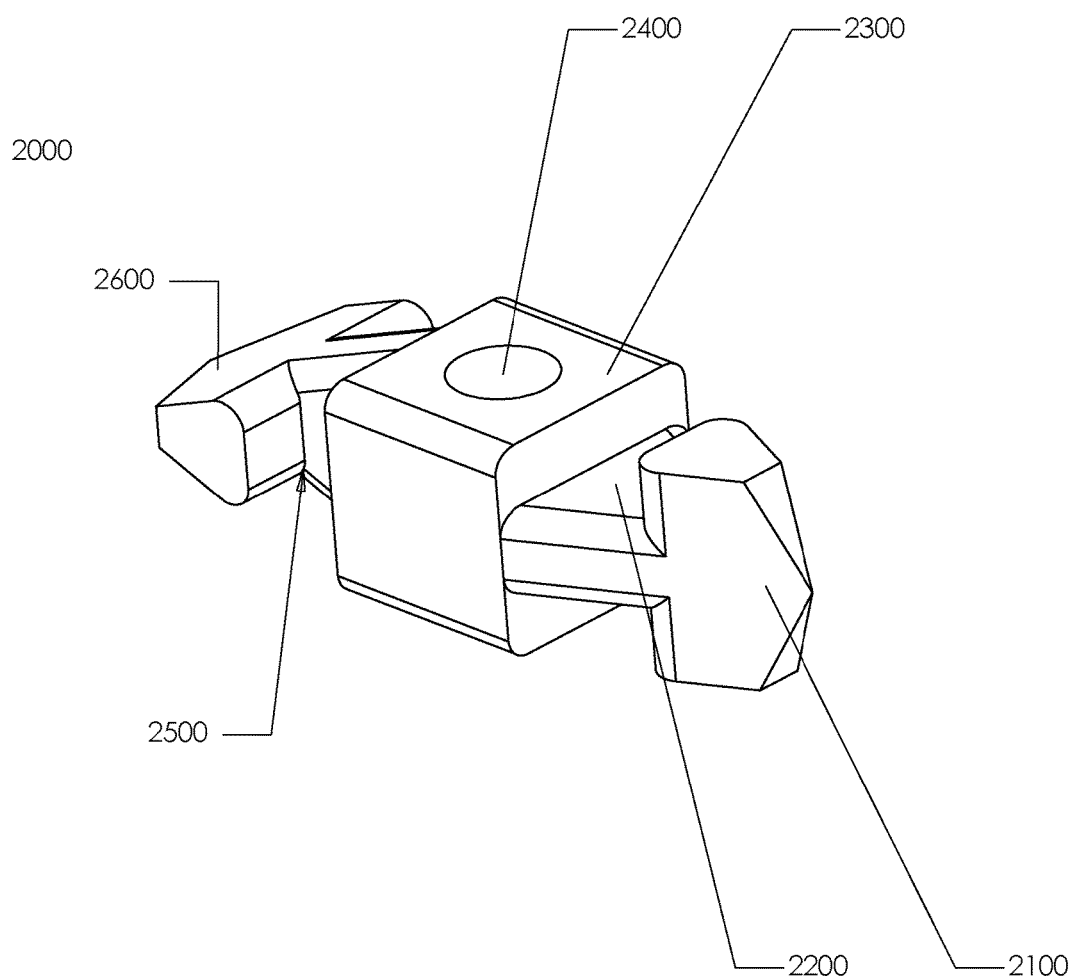
FIG. 2 shows a perspective view of a needle 2000.
Figure 3:
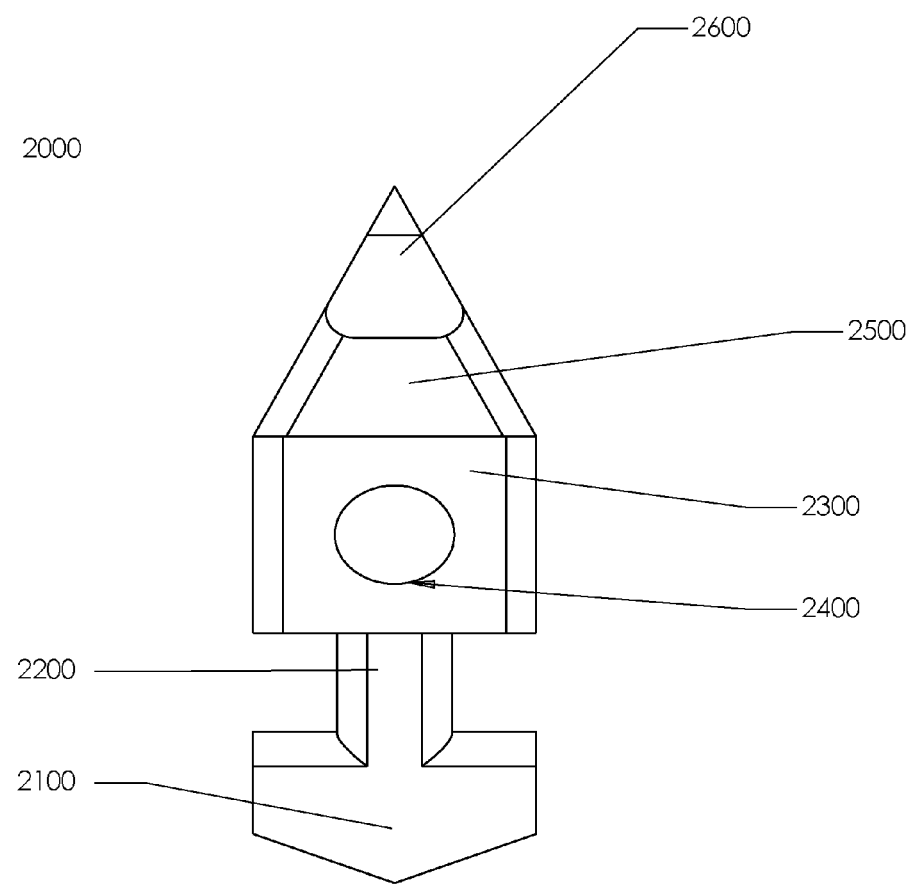
FIG. 3 shows a plan view of a needle 2000.

Referring now to FIGS. 2 and 3 together, a first embodiment 2000 of a needle is shown. Needle 2000 is an elongated body having sharp points 2100 and 2600 at opposing ends thereof. About the medial portion 2300 of needle 200 there is an aperture 2400 sized and shaped to accommodate a portion of suture, including for instance 0-0 resorbable monofilament suture or another suture known in the surgical arts. There are mating features 2200 and 2500 disposed about respective ends 2100 and 2600 of the needle.

Referring still to FIG. 3, the orientation of needle 2000 has been chosen to demonstrate that features 2500 disposed near end 2600 of needle 2000 include sloped faces meeting at a point and that features 2200 near end 2100 include a stepped shoulder. If needle 2000 as it is shown were rotated 90 degrees about its long axis, a similar stepped shoulder of features 2500 as well as a sloped face of features 2200 would become visible.

Figure 4A:
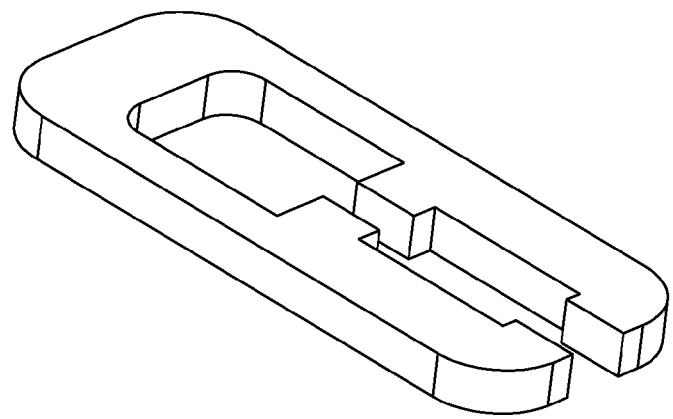
FIG. 4a shows a perspective view of a clip 1500.
Figure 4B:
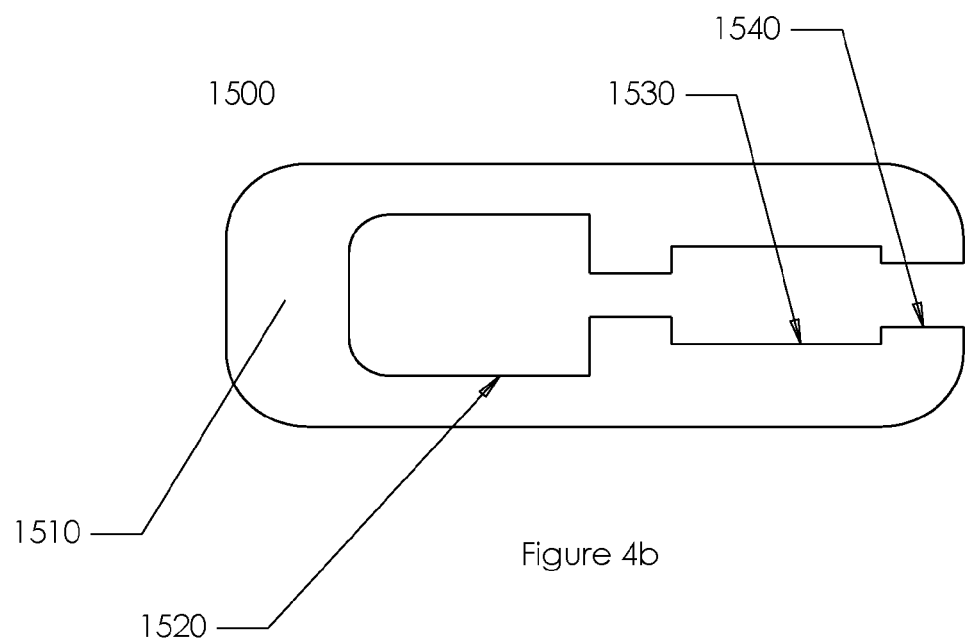
FIG. 4b shows a top view of a clip 1500.

Referring now to FIGS. 4a and 4b together, a clip 1500 is shown. Clip 1500 is a substantially planar elongated member having a grasping portion 1530 at an anterior end thereof sized and shaped to be engaged upon the stepped shoulder of features 2200 or 2500. There is a fitment groove 1520 disposed upon the posterior end portion of clip 1500 sized and shaped to retain the clip within a jaw. There is a spring portion 1510 disposed upon the posterior-most portion of clip 1500 which provides a biasing force returning clip 1500 to its resting condition when anterior tips 1540 are separated from one another. Clip 1500 may be made from a flexible material including for instance a metal such as spring steel or a polymer such as nylon.

Figure 5A:
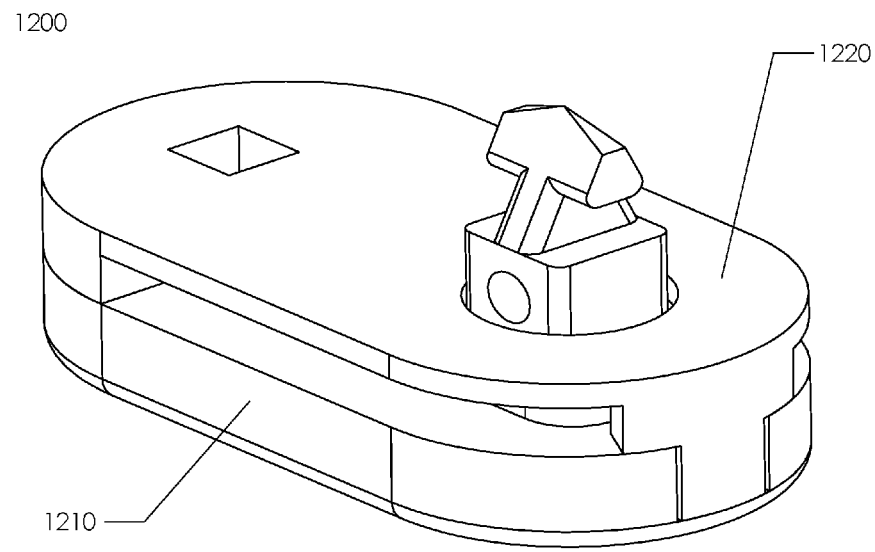
FIG. 5a shows a perspective view of a lower jaw 1200 with a needle 1500 inserted therein.
Figure 5B:
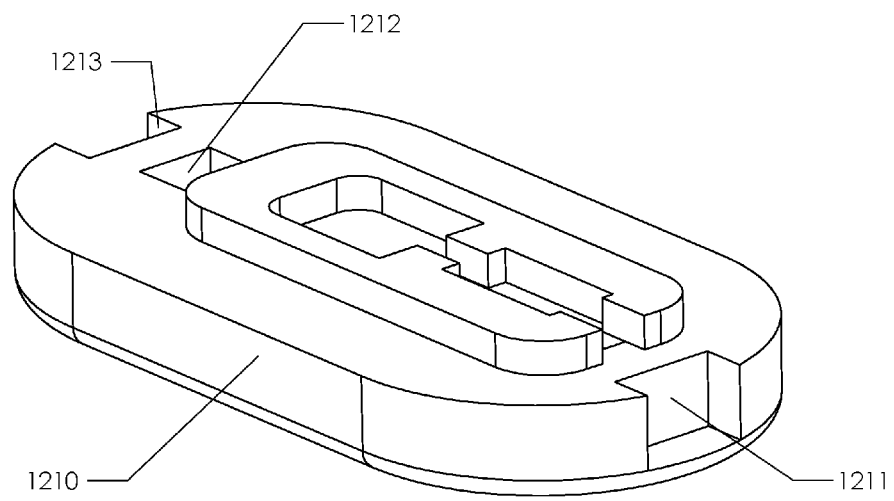
FIG. 5b shows a perspective view of a distal jaw 1200 with the cover 1220 removed.
Figure 5C:
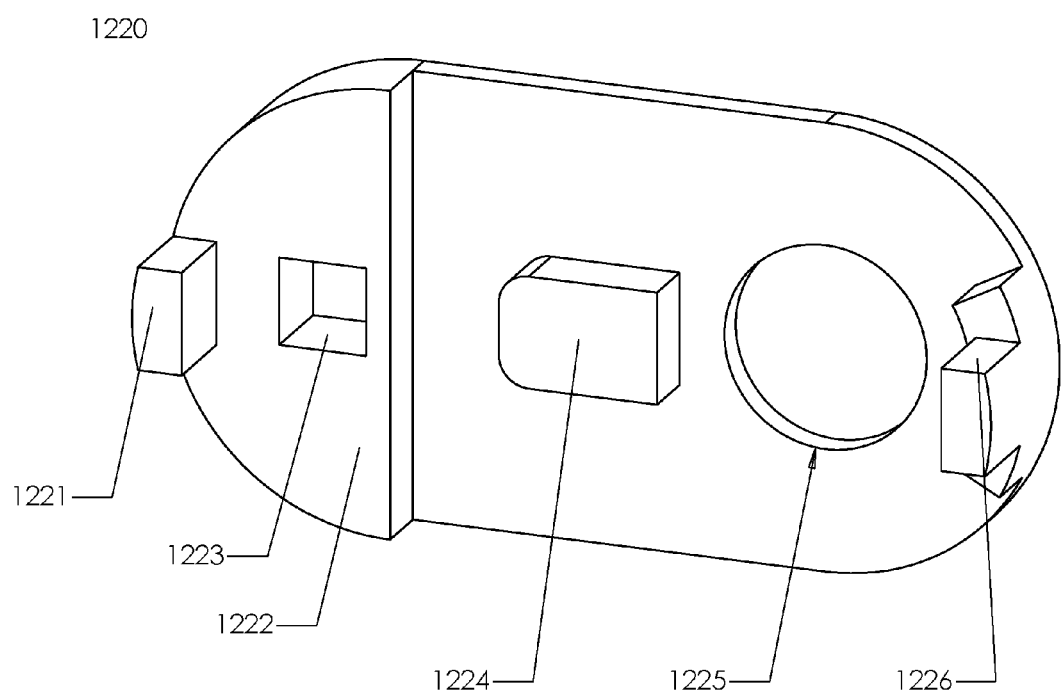
FIG. 5c shows a perspective view of the cover 1220 of a distal jaw 1200.

Referring now to FIGS. 5a, 5b, and 5c together a distal jaw 1200 is shown having a needle 2000 removably inserted therein. Jaw 1200 has a distal jaw body 1210 and a cover 1220. Jaw body 1210 has an aperture 1212 extending substantially therethrough sized and shaped to accommodate a plunger shaft (described later) as well as clip grooves 1213 and 1211 disposed about the respective posterior and anterior ends thereof. Cover 1220 has clip portions 1221 and 1226 sized and shaped to mate with and couple to clip grooves 1213 and 1211. There is an aperture 1223 that is sized and shaped to accommodate a plunger shaft as well as a clip retainer 1224 sized and shaped to fit within fitment groove 1500 as well as an aperture 1225 size and shaped to allow needle 2000 to rotate freely about the needle's long axis when the needle disposed within the aperture. There is a well disposed within distal jaw body 1210 corresponding to aperture 1225, wherein the bottom of the well is sized and shaped to define the limit of the needle 2000's travel into the body.

Figure 6A:
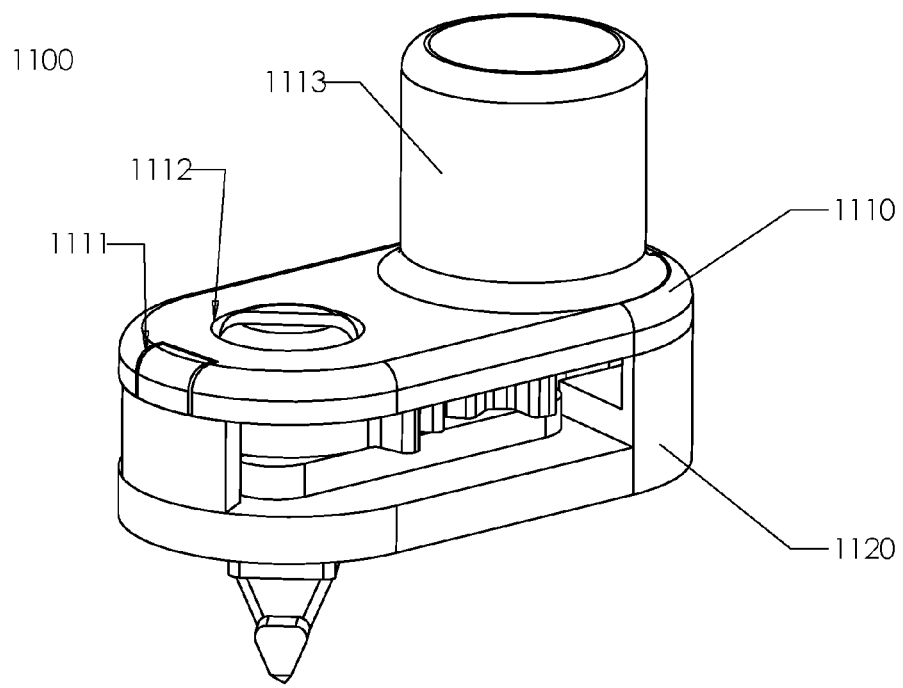
FIG. 6a shows a perspective view of a proximal jaw 1100.
Figure 6B:
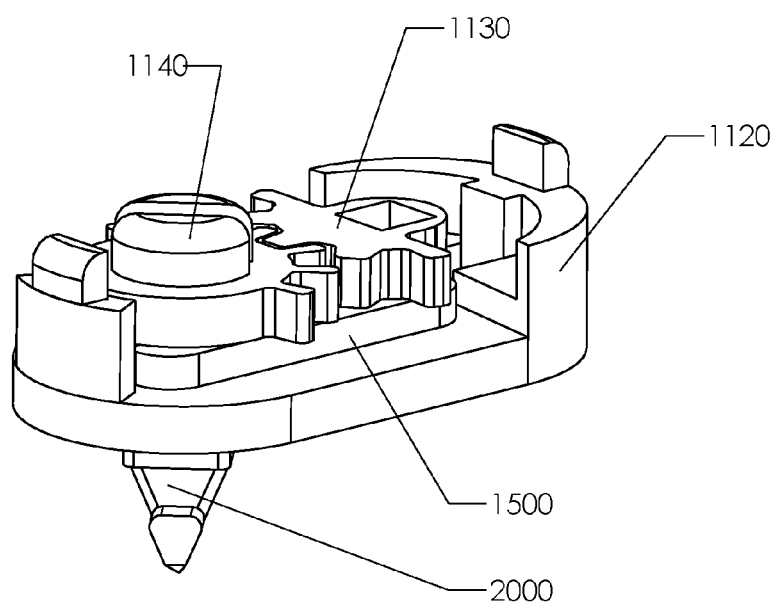
FIG. 6b shows a perspective view of a proximal jaw 1100 with its cover removed.

Referring now to FIGS. 6*a* and 6*b* together a proximal jaw 1100 is shown having a base 1120 and a cover 1110. Cover 1110 has a sleeve 1113 sized and shaped to accommodate shaft 1300 therein. There are two rotating gears coupled to base 1120. These are driver 1140 and pivot 1130. Pivot 1130 has an aperture disposed upon the posterior end thereof sized and shaped to retain a rotator shaft (described later) therewithin and gears disposed about the anterior portion thereof sized and shaped to be radially engaged upon complementary gears disposed about driver 1140. There is a clip 1500 disposed distally from the gears which is oriented to retain a needle 2000 therein similarly to the arrangement of the distal jaw 1200.

Figure 7:
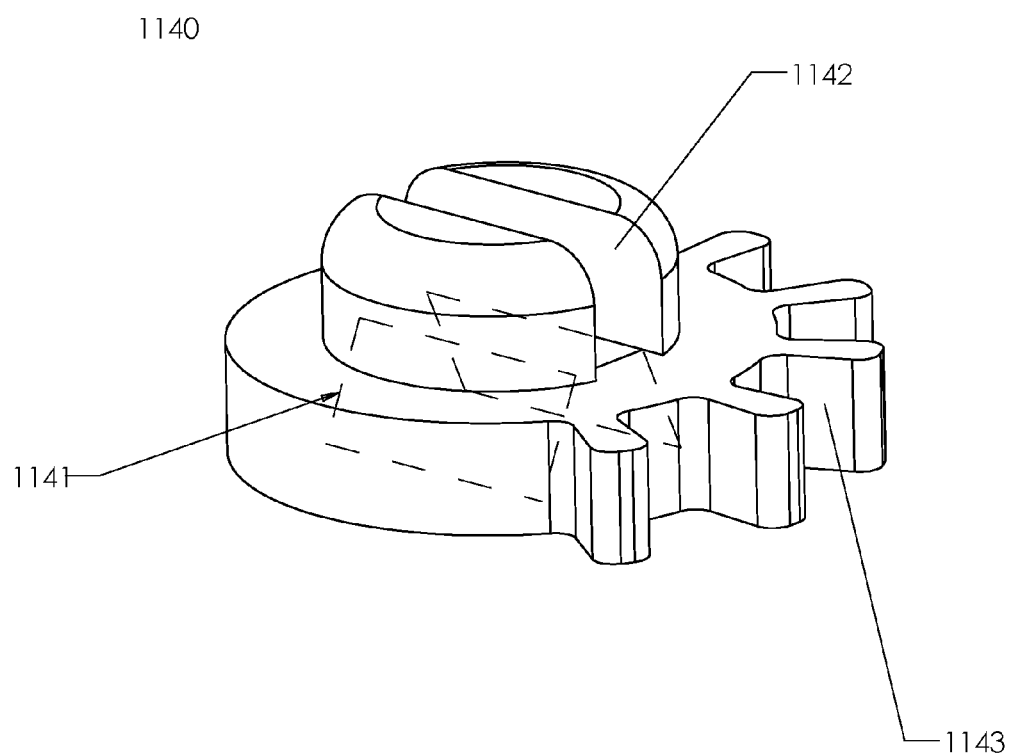
FIG. 7 shows a perspective view of a drive gear 1140.

Referring now to FIG. 7, a driver 1140 is shown with interior sloped faces 1141 denoted by dashed lines. Faces 1141 are sized and shaped to abut the inclined faces of needle 2000. There are radial gears 1143 disposed about a portion of the circumference of driver 1140 sized and shaped to be rotationally engaged upon complementary gears on pivot 1130. There is an extrusion 1142 extending proximally from the body of drive 1140 whose outer perimeter is substantially round and sized and shaped to rotate within a complementary aperture in cover 1110, thereby defining a bearing surface.

In the embodiment of the present disclosure shown in the figures, features 2500 and 2200 are oriented at an angle theta from one another with theta equal to 90 degrees. Features 2500 and 2200 are sized and shaped to selectably interfere with the features of clips 1500 disposed in the jaws. The purpose of this arrangement is so that when needle 2000 is disposed within the jaws one end of the needle is engaged to a jaw by means its stepped shoulder while the other end of the needle exposes its sloped sides to the engagement portion of remaining jaw. When needle 2000 is rotated theta degrees within the jaws this relationship is reversed and the first end of the needle becomes disengaged from its jaw while the second end of the needle now becomes engaged. Although theta is shown as being 90 degrees, it could be any non-zero value and still remain within the scope of the present disclosure and its appended claims.

Although the features of the present disclosure are shown and described with the respective clips 2000 disposed within each of jaws 1200 and 1100 in alignment and the features at opposing ends of needle 2000 having an angular offset theta therebetween, there are further embodiments of the present disclosure wherein the features of the needle are in alignment and the respective orientation of clips has a non-zero angle zeta therebetween.

Figure 8:
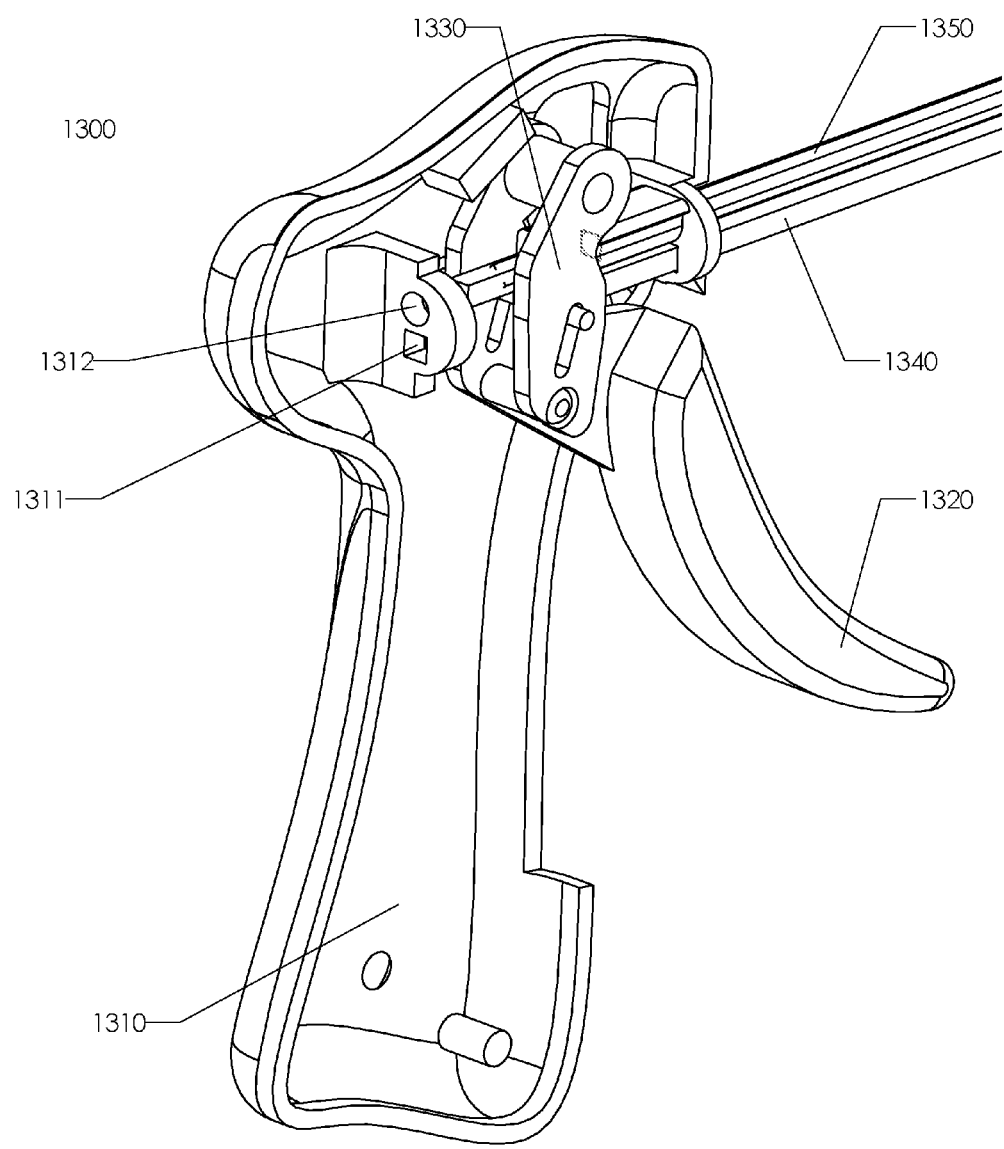
FIG. 8 shows a perspective view of a handle 1300 with its cover removed.

Referring now to FIG. 8, a handle 1300 is shown with its cover removed. Handle 1300 has a plunger shaft 134*o* and rotator shaft 1350 extending therefrom and situated within respective apertures 1311 and 1312 within the body of handle 1300. Plunger shaft is able to slide proximally/distally within aperture 1311 and rotator shaft 1312 is able to rotate about its longitudinal axis within aperture 1312. Plunger shaft 1340 is coupled to and drives the distance between the jaws. Rotator shaft 1350 is coupled to and drives the rotation and orientation of the needle within the jaws.

Plunger shaft 1340 is slideably coupled to the body of handle 1300 via apertures disposed in the handle which define the travel of the plunger shaft. Plunger shaft 1430 is also pivotably coupled to a trigger 1320 which is itself also pivotably coupled to handle 1300. Thereby, urging the trigger 1320 towards the body of handle 1300 and reducing the distance therebetween also displaces the plunger shaft proximally. According to certain embodiments of the present disclosure, there is a spring or other biasing member coupled between trigger 1320 and handle 1300 which urges the trigger away from the handle, thereby resetting the handle into a resting position at its furthest point from the body and the jaws of the device at their furthest possible distance from one another.

Figure 9:
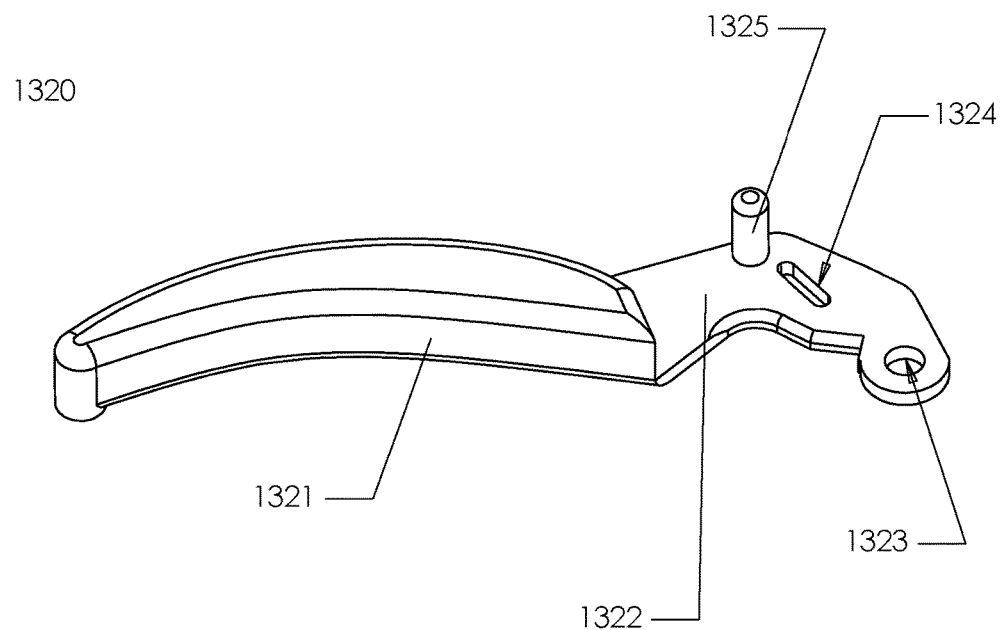
FIG. 9 shows a perspective view of a trigger 1320.

Referring now to FIGS. 8 and 9 together, a trigger 1320 is shown. Trigger 1320 has a distal face 1321 sized and shaped to be pulled by the fingers of an operator, a pivot aperture 1323 about which it moves within the handle 1300, an elongated slot 1324 which defines the travel of the pin which couples the plunger shaft to the trigger. There is also a pin 1325 extending from the face of the trigger which locates a cover plate 1330 used to keep the plunger shaft in place.

Figure 10:
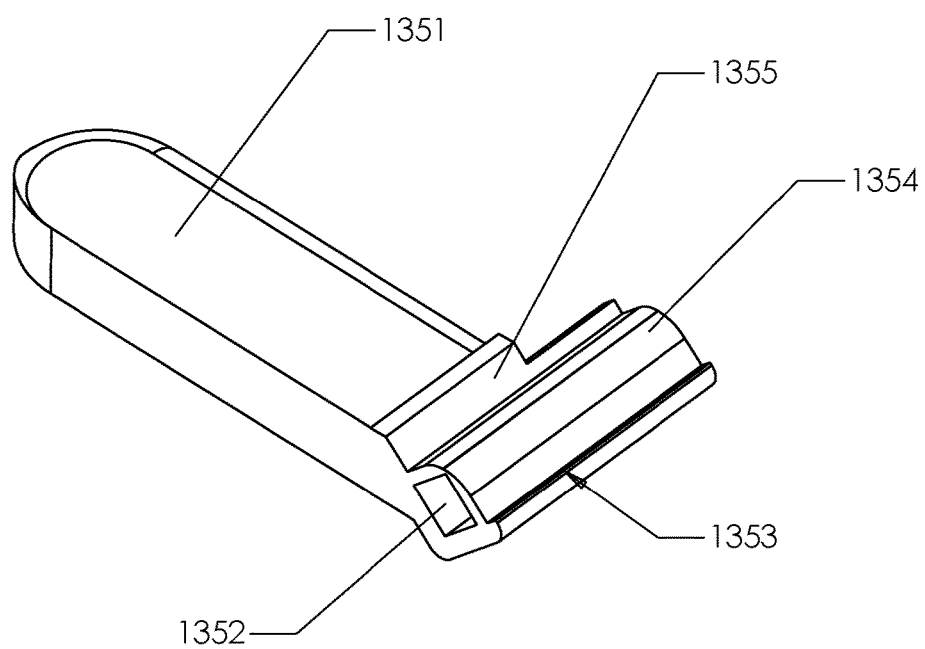
FIG. 10 shows a perspective view of a toggle 1350.

Referring now to FIG. 10, a toggle 1350 is shown. Toggle 1350 has an aperture 1352 extending therethrough sized and shaped to engage the rotator shaft 1350 therein. There are opposing faces 1355 and 1353 with a bearing surface 1354 disposed upon the toggle in co-axial relation to the rotator shaft. Faces 1355 and 1353 interfere with shaft 1340 thereby defining the limits of the travel of the toggle. According to certain embodiments of the present disclosure, including that which is shown in the figures, toggle 1350 and trigger 1320 are sized and shaped such that toggle 1350 may only by moved when trigger 1320 is depressed. This is so that the needle cannot be disengaged from its first jaw with the second jaw being ready to grasp said needle. This is achieved in the embodiment shown in the figures by the faces of cover plate 1330 and face 1322 of trigger 1320 blocking the path of the toggle unless the trigger is drawn back proximally.

Figure 11:
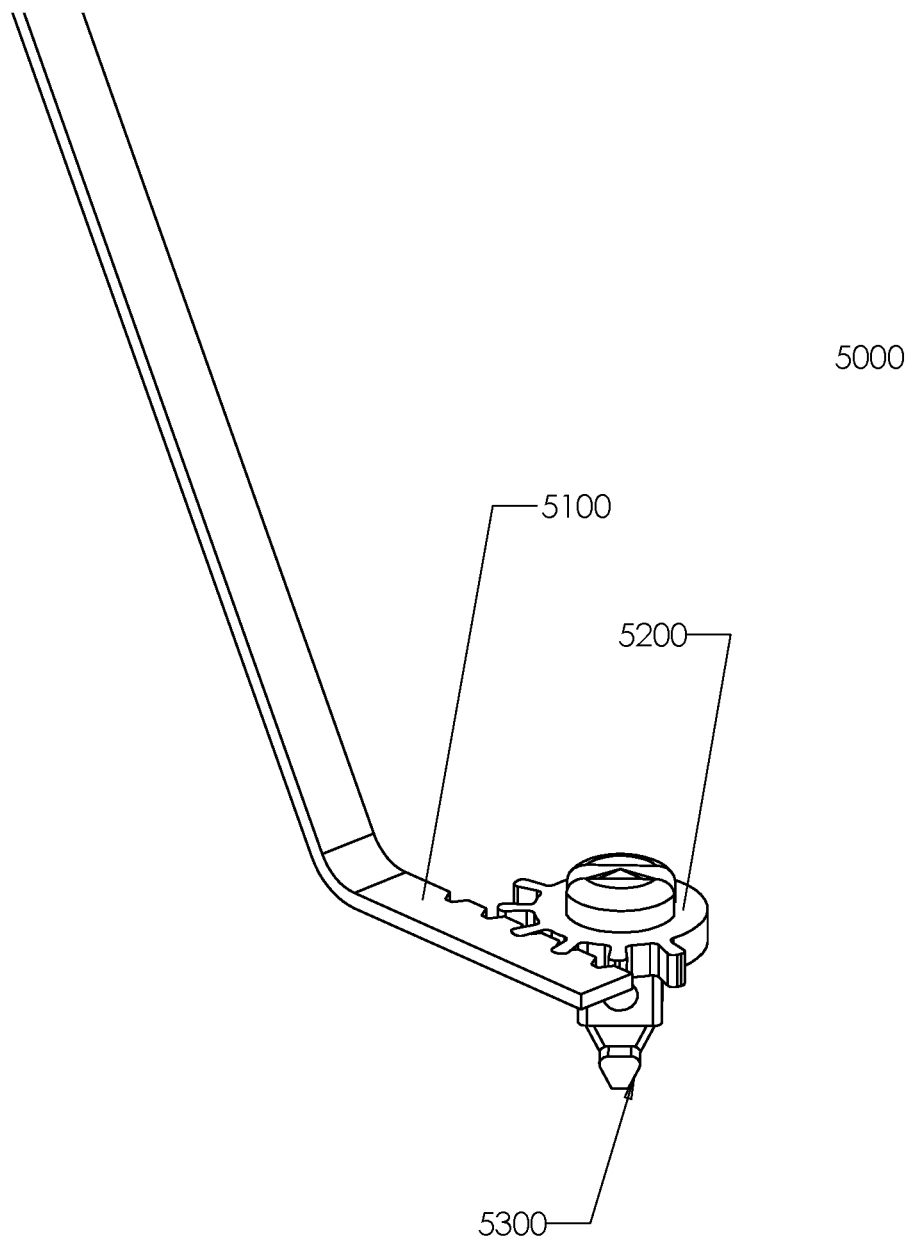
FIG. 11 shows a perspective view of a further embodiment of a driver arrangement.

Referring now to FIG. 11, a further embodiment 5000 of the present disclosure is shown, therein the function of the rotational shaft in the previous embodiment (defining the orientation of the needle and needle driver) is carried out by a flexible strip 5100. Strip 5100 is a portion of flexible metal or polymer including for instance nylon or spring steel which is slideably disposed within a tool shaft and jaw. Strip 5100 is coupled at its proximal end to a user-actuated plunger and is frictionally engaged by teeth at its distal end to a drive gear 5200 which in turn operates a needle 5300. Drive gear 5200 and needle 5300 are substantially similar in function and shape to previously described gear 1140 and needle 2000.

Although needle 2000 is shown having an aperture sized and shaped for accommodating suture, there are further embodiments of the present disclosure wherein a portion of suture is permanently affixed to a needle including for instance by means of co-molding.

A method of using a surgical tool will now be described. Initially, a surgical tool is provided in a first condition, with the needle disposed in a first jaw. Upon depression of the hand lever by an operator, the jaws are urged towards one another. Upon reaching the end of their travel, the operator may choose to flip the toggle switch on the handle, thereby rotating the needle 90 degrees and switching which jaw the needle is presently engaged into. Upon release of the hand lever, the jaws again separate although now the needle is captured in the second jaw. This general procedure may be repeated as many times as necessary. In the presence of tissue between the jaws, a needle and its accompanying suture would be drawn through the tissue, thereby facilitating suturing.

Although the structures of the previous section have been discussed with considerable detail. They are intended as but one exemplary embodiment for the implementation of the appended claimset.

What is claimed is:

1. A surgical tool having:
   a. at least a first and second jaw having complementary faces sized and shaped for grasping tissue therebetween;
      i. wherein the distance between the jaws may be modulated between a shorter-distance "closed" condition and a longer distance "open" condition;
   b. an elongated needle selectably engageable to at least one of the jaws,
      i. wherein the needle has a first mating feature selected from one of a detent, emboss, or groove disposed about a portion of the circumference near the first end the needle;
      ii. there is a complimentary opening in the first jaw sized and shaped to accommodate the first end of the needle therein and a clip disposed upon a portion of the circumference of the opening, with the being sized and shaped to have a substantially inverse shape to that of a portion of the first mating feature so as to enable mechanical coupling between the clip and the first mating feature;
      iii. wherein rotating the needle about the long axis of the needle into a configuration henceforth referred to as "A" with the first mating feature and first clip interfering with one another couples the first end of the needle to the first jaw;
      iv. wherein rotating the needle about the long axis of the needle into a configuration henceforth referred to as "B" with the first clip obscured from the first mating feature disengages the respective clips and mating features from one another and consequently disengages the needle from the first jaw;
      v. wherein there is a gear coupled to the first jaw that rotates the needle between the A and B configurations.

2. The surgical tool of claim 1,
   a. wherein the needle has a second mating feature selected from one of a detent, emboss, or groove disposed upon a portion of the circumference of the second end of the needle;
   b. wherein there is a there is a complimentary opening in the second jaw sized and shaped to accommodate the second end of the needle therein and a second clip disposed upon a portion of the circumference of the opening, with the second clip being sized and shaped to have a substantially inverse shape to that of the second mating feature so as to enable mechanical coupling between the to the second mating feature;
   c. wherein rotating the needle about the long axis of the needle into a configuration henceforth referred to as "C" with the second mating feature and second clip interfering with one another couples the second end of the needle to the second jaw;
   d. wherein rotating the needle about the long axis of the needle into a configuration henceforth referred to as "D" with the second clip obscured from the second mating feature disengages the respective clips and mating features from one another and consequently disengages the needle from the second jaw;
   e. wherein the gear rotates the needle between the C and D configurations.

3. The surgical tool of claim 2, wherein the first and second clips are substantially parallel to one another and the first and second mating features are aligned to one another such that the A and D conditions occur contemporaneously and the B and C conditions occur contemporaneously such that disengaging the needle from the first jaw engages it upon the second jaw and vice versa.

4. The surgical tool of claim 2, wherein the first mating feature and second mating feature upon the needle are aligned to one another and there are respective clips in each jaw aligned to one another such that if the needle is rotated between the A condition and B condition it is always capable of being coupled to either the first or second jaw.

5. The surgical tool of claim 1, wherein first end of the needle has at least one sloping face disposed away from the first mating feature and a complementary biasing member disposed within the first clip such that when the surgical tool is oriented in a B configuration, the force of the biasing member against the sloped face urges the needle out of the first jaw.

6. The surgical tool of claim 1, wherein the distance between the jaws is adjustable by a user of the device by means of a mechanical, hydraulic, pneumatic, or electronic coupling.

7. The surgical tool of claim 1, wherein there is stop disposed within the opening in the first jaw which limits the depth to which the first end of the needle may be inserted therewithin.

8. The surgical tool of claim 1, wherein the first clip is selected from one of a magnet, a polymer spring, a metallic spring, live-hinged spring formed into the jaw, a planar u-shaped shackle, a recessed feature, an embossed feature, piano wire, or a single sided planar slip.

9. The surgical tool of claim 1, wherein the gear catches the needle within the opening.

10. The surgical tool of claim 1, wherein the gear is driven by a rotating shaft.

11. The surgical tool of claim 1, wherein the gear is driven by an elongated flexible strip having a plurality of teeth disposed thereupon, thereby defining a rack gear.

12. The surgical tool of claim 1, wherein the gear is mechanically or electronically coupled to a stop such that it may only be turned when the jaws are configured into the "closed" condition.

13. The surgical tool of claim 1, wherein the opening is a substantially round aperture.

14. The surgical tool of claim 1, wherein the jaws are at the distal end of an elongated shaft.

15. The surgical tool of claim 14, wherein the jaws and needle are driven by mechanically coupled hand controls at the proximal end of the shaft.

16. The surgical tool of claim 1, wherein the needle has an aperture extending through a medial portion thereof with the aperture sized and shaped to securely accommodate a portion of suture therewithin.

17. The surgical tool of claim 1, wherein the needle has a portion of suture fixed to a medial portion thereof.

18. A surgical tool having:
 a. at least a first and second jaw having complementary faces sized and shaped for grasping tissue therebetween
  i. wherein the distance between the jaws may be modulated between a shorter-distance "closed" condition and a longer distance "open" condition;
 b. an elongated needle selectably engageable to at least one of the jaws,
  i. wherein the needle has a first mating feature selected from one of a detent, emboss, or groove disposed about a portion of the circumference near the first end of the needle;
  ii. there is a complimentary opening in the first jaw sized and shaped to accommodate the first end of the needle therein and a clip disposed upon a portion of the circumference of the opening, with the clip being sized and shaped to have a substantially inverse shape to that of the first mating feature so as to enable mechanical coupling between the capturing structure to the first joining structure;
  iii. wherein rotating the first mating feature about the long axis of the needle into a configuration henceforth referred to as "A" with the first mating feature and first clip interfering with one another couples the first end of the needle to the first jaw;
  iv. wherein rotating the first mating feature about the long axis of the needle into a configuration henceforth referred to as "B" with the first clip obscured from the first mating feature disengages the respective clip and mating features from one another and consequently disengages the needle from the first jaw;
  v. wherein there is a gear coupled to the first jaw that turns the needle between the A and B configurations.

\* \* \* \* \*